United States Patent [19]
DeLew

[11] 3,955,914
[45] May 11, 1976

[54] FLAME PHOTOMETRIC DETECTOR EMPLOYING PREMIXED HYDROGEN AND OXYGEN GASES

[75] Inventor: Richard Brandt DeLew, Corte Madera, Calif.

[73] Assignee: Varian Associates, Palo Alto, Calif.

[22] Filed: Jan. 15, 1975

[21] Appl. No.: 541,320

Related U.S. Application Data

[60] Division of Ser. No. 389,614, Aug. 20, 1973, Pat. No. 3,879,126, which is a continuation of Ser. No. 232,926, March 8, 1972, abandoned.

[52] U.S. Cl. ............................... 431/353; 356/187; 431/4
[51] Int. Cl.² ........................................ F23D 15/02
[58] Field of Search ............ 431/48, 353, 350, 352, 431/354; 356/187

[56] References Cited
UNITED STATES PATENTS

| | | |
|---|---|---|
| 2,990,749 | 7/1961 | Thiers et al. ...................... 356/87 X |
| 3,208,333 | 9/1965 | Gilbert ............................... 431/4 X |
| 3,807,863 | 4/1974 | Raillere et al. ...................... 356/87 |

*Primary Examiner*—Edward G. Favors
*Attorney, Agent, or Firm*—Stanley Z. Cole; Gerald M. Fisher; John J. Morrissey

[57] ABSTRACT

A flame photometric detector including a burner assembly having a first passageway leading to the burner tip so that a mixture of the hydrogen fuel gas and the combustion supporting gas such as oxygen may be delivered via the passageway to the burner tip to produce a hydrogen rich reducing flame. The sample to be analyzed is delivered via a second passageway and directed by a sample guide to the peripheral region of the reducing flame where the sample is burned in a relatively low temperature, hydrogen rich region whereby the interfering light emission from interfering substances is maintained at a low level.

5 Claims, 3 Drawing Figures

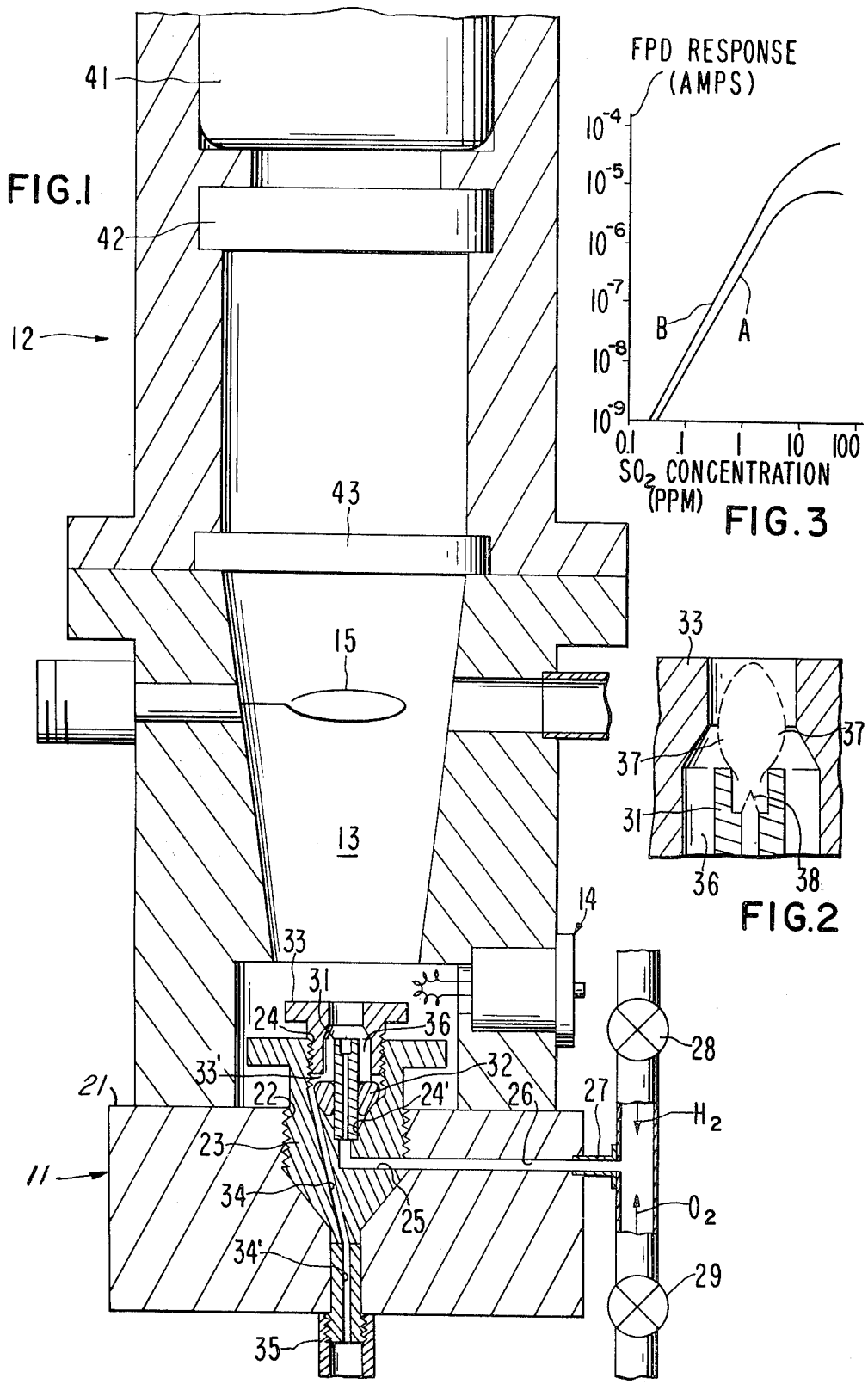

FLAME PHOTOMETRIC DETECTOR EMPLOYING PREMIXED HYDROGEN AND OXYGEN GASES

This is a division of application Ser. No. 389,614 filed on Aug. 20, 1973, now U.S. Pat. No. 3,879,126, which was a continuation of application Ser. No. 232,926 filed on Mar. 8, 1972 abandoned.

BACKGROUND OF THE INVENTION

Flame photometric detectors are now in common use as relatively inexpensive spectroscopic detectors for use with gas chromatographs, particularly for the analysis of sulfur and phosphorus substances in the effluent from the gas chromatograph. As described in an article entitled "Gas Chromatographic Detectors" by C. H. Hartmann in Analytical Chemistry, Vol. 43, No. 2, pages 113A to 125A, February 1971, the basic elements of the flame photometric detector include a burner jet where the sample of effluent from the GC is burned or heated in the combustion provided by $H_2$ fuel gas and a combustion supporting gas such as oxygen or air, and a spectrophotometer for observing the sample including a suitable light filter and photodetector. When substances containing sulfur are brought into contact with the hydrogen rich flame, they emit a characteristic light spectrum at about 360–410 nm; phosphorus-containing substances produce light emission centered about 526 nm.

In the known form of such detectors, as illustrated by the structures shown in U.S. Pat. No. 3,290,118 issued Dec. 6, 1966 to C. Van Der Smissen entitled "Apparatus For Detecting Phosphorus And/Or Sulfur In Gases" and U.S. Pat. No. 3,489,498 issued Jan. 13, 1970 to S. Brody et al. entitled "Flame Photometric Detector With Improved Specificity To Sulfur And Phosphorus", the sample under test, for example air or the column effluent from a gas chromatograph mixed with the combustion supporting gas such as oxygen or air, is delivered to the burner tip through a first tube or passageway. The hydrogen is delivered to the burner housing via a separate passageway where it burns with the sample gas and oxygen and produces the desired combustion.

The flame produced by such a device may not be reliable in operation since, for example, it is subject to blowout resulting from a sudden surge of solvent in the effluent from the chromatograph and a resultant oxygen starvation. In addition, should the column output including the oxygen source be disconnected from the detector input, the flame is extinguished and the hydrogen may escape and create a safety hazard.

Additionally, when the sample and carrier gas are fed into the very hot center portion of the hydrogen and oxygen flame, the burning of substances such as organic compounds which may be present results in an interfering light emission, reducing the specificity of the detector, i.e., the ability to respond primarily to a select group or groups of substances with a minimal response to all other substances. Special efforts have been employed in the past in an effort to block this interfering light emission from the spectrophotometer; for example, in U.S. Pat. No. 3,489,498 a cylindrical shield is provided about the tip of the burner so that the lower portion of the flame where such interference-producing burning normally takes place is not in the optical line of sight of the photospectrometer so that such interfering light emission will not degrade the selectivity. However, blocking the emitted light in this fashion tends to reduce detector sensitivity, i.e., the effectiveness of the detector as a transducer in converting the sample into a measurable electrical signal, since it also blocks a portion of the desired emission.

SUMMARY OF THE PRESENT INVENTION

The present invention provides a novel flame photometric detector wherein the hydrogen fuel gas and the combustion supporting gas, e.g., oxygen, are premixed and then delivered to the burner tip via one passageway to produce the desired reducing flame at the tip. The sample is delivered to the peripheral region of the flame via a separate passageway such that contact of the sample occurs in the outer portion of the flame. As a result, the flame is considerably more reliable and not snuffed out with surges of solvent through the sample conduit. In fact, the flame continues even when the gas chromatograph column is removed. As a consequence of this premixing, there is no free-flowing hydrogen to escape.

Since the sample is introduced into the peripheral region of the flame, it is burned or heated in a cooler portion of the hydrogen-rich flame and this results in the substances of interest being burned or heated at optimum conditions, including temperature and hydrogen concentration, while at the same time the interfering substances are being burned or heated at non-optimum conditions for them. This results in minimum interfering light emission, and thus a more encompassing view of the flame may be provided to the spectrophotometer.

DESCRIPTION OF THE DRAWINGS

FIG. 1 is a longitudinal cross section view of a preferred form of flame photometric detector structure of the present invention.

FIG. 2 is an enlarged view of the tip region of the burner assembly region of FIG. 1.

FIG. 3 is a response curve for a prior art detector and the detector of the present invention.

DESCRIPTION OF THE PREFERRED EMBODIMENTS

Referring now to the drawings, the detector comprises a generally elongated body structure including the burner means 11 mounted in one end thereof, the photospectrometer structure 12 mounted in the opposite end thereof, and the combustion chamber 13 positioned therebetween. As with standard forms of flame photometric detectors, the structure is provided with a suitable igniter assembly 14 for igniting the flame, and an ion collector means 15 for monitoring hydrocarbons within the chamber 13.

The burner means comprises a mounting base 21 having a threaded bore 22 therein and a cylindrical burner base 23 threaded into the bore in the mounting base. The burner base 23 is provided with an axial bore 24 therein, the bore being internally threaded at its top end and tapering down into a smaller diameter bore 24' near the lower end where it is provided with a flow passage bore 25. This bore 25 mates with a bore 26 leading out through the mounting base 21 to a T connection tubing 27, the two branches of the tubing being fed via control needle valves 28 and 29 from the sources of hydrogen and oxygen, respectively.

A burner tip assembly is mounted in the bore within the burner base and comprises a hollow cylindrical flame tip member 31, a brass ferule 32, and a hollow cylindrical nut 33 forming a sample guide member. The hollow cylindrical flame tip member 31 is nested at one end into the lower end of the bore 24' in the burner base 23, the flame tip member being engaged by the annular ferule 32 which is urged downwardly against the outer wall of the flame tip member 31 and the inner wall of the burner base 23 by the hollow cylindrical sample guide 33 threaded into the bore in the burner base. A bore 34 extends through the burner base 23 from the lower end thereof, this bore mating with a bore 34' in the base 21 where it connects with a conduit 35 serving as the sample input. The bore 34 leads into the annular chamber 36 formed between the inner wall of the sample guide 33 and the outer wall of the flame tip member 31. The sample guide 33 is provided with notches 33' in its threaded inner end to provide good ingress from the bore 34 to the annular chamber 36.

In operation, the hydrogen fuel gas and the combustion supporting gas, i.e., oxygen, are delivered via the needle valve controls 28 and 29 to the flow passage tubing 27 where they are mixed and then brought into the bore 26 in the mounting base, passing up through the central bore in the flame tip member 31 to the end of the tip member where the gases are ignited by a suitable flame igniter 14 to form the hydrogen-rich flame. The sample including the carrier from the chromatographic column is introduced through the bore 34 in the lower end of the burner base 23 and passes around the upper portion of the ferrule 32 and into the chamber 36 surrounding the flame tip 31. The sample is then directed by the sample guide 33 into the peripheral region of the reducing flame, i.e., the lower temperature hydrogen-rich region. The temperature of this region is in the order of 400°C, as distinguished from the temperature in the oxidation region of the flame of the order of 1700°C. While burning or heating of the substances of interest is optimized at this hydrogen-rich 400°C region to give good light emission therefrom, the undesired interference substances, such as hydrocarbons, are not burned efficiently. Thus, the interfering light emissions are maintained at a relatively low value.

The photospectrometer unit 12, comprising the standard photomultiplier tube 41, light filter 42, and explosion shield 43, is positioned above and in axial alignment with the axis of the burner assembly to give a full end-on viewing of the flame in accordance with the teachings of the U.S. patent application of C. Hartmann filed concurrently herewith and entitled "Flame Photometric Detector With End-On Flame Viewing". It should be understood that the combustion region may also be viewed from the side as with the standard existing forms of photometric flame detector, and the benefit of lower interfering emissions stemming from the improved burner design will still be obtained.

Referring to FIG. 3, there are shown two curves representing the flame photometric detector response in amps for a standard known form of detector (curve A) and for a detector employing the heater of the present invention (curve B) obtained with different steady state levels of sulfur dioxide burned as the sample. Although the response is higher for the detector described herein, a higher noise level was also obtained so that the net detectivity of the two devices is about the same. While the prior art detector represented by curve A exhiits a limit to dynamic range at about 20 ppm, the detector described herein as represented by curve B has a dynamic range reaching at least to 50 ppm.

The novel combination of the burner assembly of this invention with the end-on spectrophotometer viewing technique of the above cited C. Hartmann application is shown and described in a U.S. patent application filed concurrently herewith by R. DeLew and C. Hartmann entitled "Flame Photometric Detector Employing Premixed Hydrogen and Oxygen Gases for Sample Combustion With End-On Spectrophotometer Viewing of The Flame."

What is claimed is:

1. A spectral flame burner for the detection of phosphorus and sulphur in a sample gas, said burner comprising a hollow cylindrical flame tip member, means for transmitting a mixture of combustible and combustion-supporting gases through said said flame tip member to the region adjacent one end of said flame tip member, said gaseous mixture being capable of supporting a hydrogen-rich flame in said region adjacent said flame-supporting end of said flame tip member, means defining a passageway extending around said flame-supporting end of said flame tip member whereby said flame can be maintained within said passageway, and means for transmitting said sample gas into said passageway to the side peripheral region of said hydrogen-rich flame, there being no communication between said means for transmitting said mixture of combustible and combustion-supporting gases and said means for transmitting said sample gas except in said region adjacent said flame-supporting end of said flame tip member.

2. A flame burner for producing discernible spectral lines for phosphorus and sulphuur, said burner comprising means for forming a mixture of a combustible gas and a combustion-supporting gas, said mixture being capable of supporting a hydrogen-rich flame when ignited, the side peripheral region of said flame being cooler than the interior of said flame, a flame tip member, first conduit means for introducing said mixture of combustible and combustion-supporting gases into a region adjacent said flame tip member, means for igniting said mixture of combustible and combustion-supporting gases so as to form a hydrogen-rich flame in said region adjacent said flame tip member, and second conduit means for introducing a sample gas to the side peripheral region of said flame, said first and second conduit means being arranged so that there is no communication therebetween except in said region adjacent said flame tip member.

3. The flame burner of claim 2 further comprising means for shielding said flame from the ambient atmosphere.

4. The flame burner of claim 2 wherein said flame tip member comprises a hollow cylindrical structure, the interior thereof being a portion of said first conduit means.

5. The flame burner of claim 2 wherein said second conduit means comprises a hollow cylindrical sample gas guide structure disposed circumjacent and spaced apart from said flame tip member.

* * * * *

UNITED STATES PATENT AND TRADEMARK OFFICE
CERTIFICATE OF CORRECTION

PATENT NO. : 3,955,914
DATED : May 11, 1976
INVENTOR(S) : Richard Brandt DeLew

It is certified that error appears in the above—identified patent and that said Letters Patent are hereby corrected as shown below:

Column 2, line 14:  After "sample" insert --and the flame--.

Column 2, line 68:  Change "ferule" to --ferrule--.

Column 3, line 4:   Change "ferule" to --ferrule--.

*Signed and Sealed this*

Twentieth *Day of* July 1976

[SEAL]

*Attest:*

RUTH C. MASON
*Attesting Officer*

C. MARSHALL DANN
*Commissioner of Patents and Trademarks*